US009757067B1

(12) United States Patent
Gharib et al.

(10) Patent No.: US 9,757,067 B1
(45) Date of Patent: Sep. 12, 2017

(54) SYSTEMS AND METHODS FOR PERFORMING NEUROPHYSIOLOGIC MONITORING DURING SPINE SURGERY (71) Applicant: NuVasive, Inc., San Diego, CA (US)

(72) Inventors: James Gharib, San Diego, CA (US); Robert Snow, Phoenix, MD (US)

(73) Assignee: NuVasive, Inc., San Diego, CA (US)

( * ) Notice: Subject to any disclaimer, the term of this patent is extended or adjusted under 35 U.S.C. 154(b) by 117 days.

(21) Appl. No.: 13/830,120

(22) Filed: Mar. 14, 2013

Related U.S. Application Data (60) Provisional application No. 61/724,342, filed on Nov. 9, 2012.

(51) Int. Cl.
A61B 5/00 (2006.01)
A61B 17/34 (2006.01)
A61B 5/05 (2006.01)

(52) U.S. Cl.
CPC .............. A61B 5/4893 (2013.01); A61B 5/05 (2013.01); A61B 2017/3405 (2013.01)

(58) Field of Classification Search
None
See application file for complete search history.

(56) References Cited

U.S. PATENT DOCUMENTS

| 208,227 | A | 9/1878 | Dorr |
| 972,983 | A | 10/1910 | Arthur |
| 1,194,319 | A | 8/1916 | Pretts |
| 1,328,624 | A | 1/1920 | Graham |
| 1,548,184 | A | 8/1925 | Cameron |
| 2,693,795 | A | 11/1954 | Grieshaber |
| 2,704,064 | A | 3/1955 | Fizzell et al. |
| 2,736,002 | A | 2/1956 | Oriel |
| 2,807,259 | A | 9/1957 | Guerriero |
| 2,808,826 | A | 10/1957 | Reiner et al. |
| 3,364,929 | A | 1/1968 | Ide et al. |
| 3,467,079 | A | 9/1969 | James |
| 3,509,873 | A | 5/1970 | Karlin |
| 3,587,583 | A * | 6/1971 | Greenberg ............... A61B 5/06 604/362 |
| 3,664,329 | A | 5/1972 | Naylor |
| 3,680,546 | A | 8/1972 | Asrican |

(Continued)

FOREIGN PATENT DOCUMENTS

| CA | 1142826 | 3/1983 |
| CN | 203506775 | 4/2014 |

(Continued)

OTHER PUBLICATIONS

"Electromyography System," International Search Report from International Application No. PCT/US00/32329, dated Apr. 27, 2001, 9 pages.

(Continued)

Primary Examiner — Devin Henson
Assistant Examiner — Matthew Kremer
(74) Attorney, Agent, or Firm — Stephen H. Hall; Kimberly Vines; Bradley Arant Boult Cummings LLP (57) ABSTRACT This disclosure describes a surgical instrument comprising a combination femoral nerve localizer and needle placement guide instrument. The instrument may be used with a neuromonitoring system to localize and monitor the femoral nerve during a spinal procedure.

11 Claims, 4 Drawing Sheets (56) References Cited

U.S. PATENT DOCUMENTS

| | | |
|---|---|---|
| 3,682,162 A | 8/1972 | Colyer |
| 3,724,449 A | 4/1973 | Gauthier |
| 3,740,839 A | 6/1973 | Otte |
| 3,785,368 A | 1/1974 | McCarthy et al. |
| 3,830,226 A | 8/1974 | Staub |
| 3,851,641 A | 12/1974 | Toole et al. |
| 3,888,117 A | 6/1975 | Lewis |
| 3,957,036 A | 5/1976 | Normann |
| 3,998,217 A | 12/1976 | Trumbull |
| 4,010,741 A | 3/1977 | Gauthier |
| 4,099,519 A | 7/1978 | Warren |
| 4,156,424 A | 5/1979 | Burgin |
| 4,164,214 A | 8/1979 | Stark et al. |
| 4,165,746 A | 8/1979 | Burgin |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,617,916 A | 10/1986 | LeVahn |
| 4,627,421 A | 12/1986 | Symbas |
| 4,633,889 A | 1/1987 | Talalla et al. |
| 4,658,835 A | 4/1987 | Pohndorf |
| 4,726,356 A | 2/1988 | Santilli |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,813,401 A | 3/1989 | Grieshaber |
| 4,892,105 A | 1/1990 | Prass |
| 4,926,865 A | 5/1990 | Oman |
| 4,945,896 A | 8/1990 | Gade |
| 4,955,884 A | 9/1990 | Grossi |
| 4,962,766 A | 10/1990 | Herzon |
| 4,964,411 A | 10/1990 | Johnson et al. |
| 5,007,902 A | 4/1991 | Witt |
| 5,052,374 A | 10/1991 | Alvarez-Jacinto |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,152,279 A | 10/1992 | Wilk |
| 5,161,533 A | 11/1992 | Prass et al. |
| 5,195,505 A | 3/1993 | Josefsen |
| 5,196,015 A | 3/1993 | Neubardt |
| 5,199,419 A | 4/1993 | Remiszewski |
| 5,220,920 A | 6/1993 | Gharib |
| 5,231,974 A | 8/1993 | Giglio |
| RE34,390 E | 9/1993 | Culver |
| 5,255,691 A | 10/1993 | Otten |
| 5,280,782 A | 1/1994 | Wilk |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,327,902 A | 7/1994 | Lemmen |
| 5,333,618 A | 8/1994 | Lekhtman et al. |
| 5,339,801 A | 8/1994 | Poloyko |
| 5,375,067 A | 12/1994 | Berchin |
| 5,375,481 A | 12/1994 | Cabrera |
| 5,383,876 A | 1/1995 | Nardella |
| 5,450,845 A | 9/1995 | Axelgaard |
| 5,474,056 A | 12/1995 | Laborie |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,520,610 A | 5/1996 | Giglio |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,599,279 A | 2/1997 | Slotman |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,758,643 A | 6/1998 | Wong et al. |
| 5,759,159 A | 6/1998 | Masreliez |
| 5,772,583 A | 6/1998 | Wright |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,647 A | 7/1998 | Tompkins |
| 5,785,658 A | 7/1998 | Benaron et al. |
| 5,797,854 A | 8/1998 | Hedgecock |
| 5,806,522 A | 9/1998 | Katims |
| 5,807,270 A | 9/1998 | Williams |
| 5,807,272 A | 9/1998 | Kun et al. |
| 5,814,073 A | 9/1998 | Bonutti |
| 5,830,150 A | 11/1998 | Palmer et al. |
| 5,830,151 A | 11/1998 | Hadzic et al. |
| 5,851,191 A | 12/1998 | Gozani et al. |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,902,231 A | 5/1999 | Foley et al. |
| 5,902,233 A | 5/1999 | Farley |
| 5,928,139 A | 7/1999 | Koros et al. |
| 5,928,158 A | 7/1999 | Aristides |
| 5,928,159 A | 7/1999 | Eggers et al. |
| 5,935,131 A | 8/1999 | Bonutti |
| 5,938,688 A | 8/1999 | Schiff |
| 5,944,658 A | 8/1999 | Koros |
| 5,947,896 A | 9/1999 | Sherts |
| 5,947,964 A | 9/1999 | Eggers et al. |
| 5,976,094 A | 11/1999 | Gozani |
| 6,004,262 A | 12/1999 | Putz et al. |
| 6,011,985 A | 1/2000 | Athan |
| 6,024,696 A | 2/2000 | Hoftman |
| 6,026,323 A | 2/2000 | Skladnev et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,050,996 A | 4/2000 | Schmaltz |
| 6,074,343 A | 6/2000 | Nathanson |
| 6,083,154 A | 7/2000 | Liu |
| 6,099,468 A | 8/2000 | Santilli |
| 6,104,957 A | 8/2000 | Alo et al. |
| 6,104,960 A | 8/2000 | Duysens et al. |
| 6,119,033 A * | 9/2000 | Spigelman ............ A61B 90/17 427/429 |
| 6,119,068 A | 9/2000 | Kannonji |
| 6,120,503 A | 9/2000 | Michelson |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |

(56) References Cited

U.S. PATENT DOCUMENTS

| | | |
|---|---|---|
| 6,161,047 A | 12/2000 | King et al. |
| 6,181,961 B1 | 1/2001 | Prass |
| 6,206,826 B1 | 3/2001 | Mathews et al. |
| 6,213,940 B1 | 4/2001 | Sherts |
| 6,224,545 B1 | 5/2001 | Cocchia |
| 6,224,549 B1 | 5/2001 | Drongelen |
| 6,231,506 B1 | 5/2001 | Hu |
| 6,254,532 B1 | 7/2001 | Paolitto |
| 6,259,945 B1 | 7/2001 | Epstein et al. |
| 6,264,605 B1 | 7/2001 | Scirica |
| 6,266,558 B1 | 7/2001 | Gozani et al. |
| 6,273,853 B1 | 8/2001 | Cartier |
| 6,273,905 B1 | 8/2001 | Streeter |
| 6,283,912 B1 | 9/2001 | Hu |
| 6,292,701 B1 | 9/2001 | Prass et al. |
| 6,306,100 B1 | 10/2001 | Prass |
| 6,312,392 B1 | 11/2001 | Herzon |
| 6,322,500 B1 | 11/2001 | Sikora et al. |
| 6,325,764 B1 | 12/2001 | Griffith et al. |
| 6,334,068 B1 | 12/2001 | Hacker |
| 6,337,994 B1 | 1/2002 | Stoianovici et al. |
| 6,340,345 B1 | 1/2002 | Lees |
| 6,393,325 B1 | 5/2002 | Mann et al. |
| 6,407,335 B1 | 6/2002 | Franklin-Lees et al. |
| 6,416,480 B1 | 7/2002 | Nenov |
| 6,425,859 B1 | 7/2002 | Foley et al. |
| 6,425,901 B1 | 7/2002 | Zhu et al. |
| 6,451,015 B1 | 9/2002 | Rittman et al. |
| 6,466,817 B1 | 10/2002 | Kaula et al. |
| 6,500,128 B2 | 12/2002 | Marino |
| 6,511,423 B2 | 1/2003 | Farley |
| 6,535,759 B1 | 3/2003 | Epstein et al. |
| 6,564,078 B1 | 5/2003 | Marino et al. |
| 6,579,244 B2 | 6/2003 | Goodwin |
| 6,593,528 B2 | 7/2003 | Franklin-Lees et al. |
| 6,685,632 B1 | 2/2004 | Hu |
| 6,712,795 B1 | 3/2004 | Cohen |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,819,956 B1 | 11/2004 | DiLorenzo |
| 6,829,508 B2 | 12/2004 | Schulman et al. |
| 6,830,051 B1 | 12/2004 | Lesniak et al. |
| 6,837,851 B1 | 1/2005 | Valentini |
| 6,849,047 B2 | 2/2005 | Goodwin |
| 6,849,064 B2 | 2/2005 | Hamada |
| 6,855,105 B2 | 2/2005 | Jackson, III |
| 6,895,280 B2 | 5/2005 | Meadows et al. |
| 6,902,569 B2 | 6/2005 | Parmer et al. |
| 6,926,728 B2 | 8/2005 | Zucherman et al. |
| 6,929,606 B2 | 8/2005 | Ritland |
| 6,945,933 B2 | 9/2005 | Branch |
| 6,951,538 B2 | 10/2005 | Ritland |
| 6,994,669 B1 | 2/2006 | Gannoe |
| 7,047,082 B1 | 5/2006 | Schrom et al. |
| 7,050,848 B2 | 5/2006 | Hoey et al. |
| 7,052,457 B2 | 5/2006 | Fanous |
| 7,079,883 B2 | 7/2006 | Marino et al. |
| 7,089,059 B1 | 8/2006 | Pless |
| 7,135,020 B2 | 11/2006 | Lawes |
| 7,141,015 B2 | 11/2006 | Ruane |
| D533,875 S | 12/2006 | Miles |
| 7,160,298 B2 | 1/2007 | Lawes |
| 7,177,677 B2 | 2/2007 | Kaula et al. |
| 7,182,729 B2 | 2/2007 | Abdelgany |
| 7,207,949 B2 | 4/2007 | Miles et al. |
| 7,216,001 B2 | 5/2007 | Hacker et al. |
| 7,255,680 B2 | 8/2007 | Gharib |
| 7,374,534 B2 | 5/2008 | Dalton |
| 7,435,219 B2 | 10/2008 | Kim |
| 7,470,236 B1 | 12/2008 | Kelleher et al. |
| 7,481,766 B2 | 1/2009 | Lee |
| 7,522,953 B2 | 4/2009 | Kaula et al. |
| 7,537,565 B2 | 5/2009 | Bass |
| 7,582,058 B1 | 9/2009 | Miles |
| 7,632,269 B2 | 12/2009 | Truckai |
| 7,641,659 B2 | 1/2010 | Emstad |
| 7,657,308 B2 | 2/2010 | Miles et al. |
| 7,664,544 B2 | 2/2010 | Miles et al. |
| 7,691,057 B2 | 4/2010 | Miles et al. |
| 7,785,253 B1 * | 8/2010 | Arambula et al. ............ 600/219 |
| 7,819,801 B2 | 10/2010 | Miles et al. |
| 7,850,608 B2 | 12/2010 | Hamada |
| 7,857,813 B2 | 12/2010 | Schmitz et al. |
| 7,878,981 B2 | 2/2011 | Strother et al. |
| 7,887,538 B2 | 2/2011 | Bleich et al. |
| 7,896,815 B2 | 3/2011 | Thrope et al. |
| 7,905,840 B2 | 3/2011 | Pimenta |
| 7,920,922 B2 | 4/2011 | Gharib |
| 7,922,657 B2 | 4/2011 | Gillinov |
| 7,931,589 B2 | 4/2011 | Cohen |
| 7,931,591 B2 | 4/2011 | McCarthy |
| 7,938,830 B2 | 5/2011 | Saadat et al. |
| 7,946,982 B2 | 5/2011 | Hamada |
| 7,962,191 B2 | 6/2011 | Marino |
| 7,963,927 B2 | 6/2011 | Kelleher et al. |
| 7,976,463 B2 | 7/2011 | Dewey |
| 7,981,031 B2 | 7/2011 | Frasier |
| 8,068,912 B2 | 11/2011 | Kaula et al. |
| 8,100,828 B2 | 1/2012 | Frey |
| 8,137,284 B2 | 3/2012 | Miles |
| 8,152,714 B2 | 4/2012 | Garcia-Bengochea |
| 8,152,720 B2 | 4/2012 | Loftus |
| 8,206,293 B2 | 6/2012 | Reglos |
| 8,226,554 B2 | 7/2012 | McBride |
| 8,251,997 B2 | 8/2012 | Michelson |
| 8,255,045 B2 | 8/2012 | Gharib |
| 8,257,255 B2 | 9/2012 | Farley |
| 8,262,570 B2 | 9/2012 | White |
| 8,267,859 B2 | 9/2012 | Holmes |
| 8,287,597 B1 | 10/2012 | Pimenta |
| 8,313,430 B1 | 11/2012 | Pimenta |
| 8,328,851 B2 | 12/2012 | Curran |
| 8,343,163 B1 | 1/2013 | Arambula |
| 8,360,971 B2 | 1/2013 | Farley |
| 8,425,602 B2 | 4/2013 | Guyer |
| 8,449,463 B2 | 5/2013 | Nunley |
| 8,517,935 B2 | 8/2013 | Marchek |
| 8,562,621 B2 | 10/2013 | Mignucci |
| 8,568,306 B2 | 10/2013 | Hardenbrook |
| 8,636,655 B1 | 1/2014 | Childs |
| 8,636,656 B2 | 1/2014 | Nichter |
| 8,715,175 B2 | 5/2014 | Assaker |
| 8,790,406 B1 | 7/2014 | Smith |
| 8,821,394 B2 | 9/2014 | Hawkins |
| 8,821,396 B1 | 9/2014 | Miles |
| 8,852,090 B2 | 10/2014 | Friedrich |
| 8,876,687 B2 | 11/2014 | Jones |
| 8,876,904 B2 | 11/2014 | Pimenta |
| 8,882,661 B2 | 11/2014 | Hutton |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0134570 A1 | 9/2002 | Franklin-Lees et al. |
| 2002/0161415 A1 | 10/2002 | Cohen et al. |
| 2002/0193843 A1 | 12/2002 | Hill |
| 2003/0032966 A1 | 2/2003 | Foley et al. |
| 2003/0105503 A1 | 6/2003 | Marino |
| 2004/0181165 A1 | 9/2004 | Hoey |
| 2004/0199084 A1 | 10/2004 | Kelleher et al. |
| 2004/0203490 A1 | 10/2004 | Kaplan |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0159785 A1 | 7/2005 | Rueter |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0041243 A1 * | 2/2006 | Nayak et al. ................. 604/506 |

(56) References Cited

U.S. PATENT DOCUMENTS

| | | |
|---|---|---|
| 2006/0052828 A1 | 3/2006 | Kim et al. |
| 2006/0069315 A1 | 3/2006 | Miles et al. |
| 2006/0074278 A1 | 4/2006 | Petit |
| 2006/0166157 A1 | 7/2006 | Rahman et al. |
| 2006/0224044 A1 | 10/2006 | Marchek |
| 2006/0224078 A1 | 10/2006 | Hoey et al. |
| 2007/0016097 A1 | 1/2007 | Farquhar et al. |
| 2007/0021682 A1 | 1/2007 | Gharib et al. |
| 2007/0038033 A1 | 2/2007 | Jones |
| 2007/0156025 A1 | 7/2007 | Marchek |
| 2007/0198062 A1 | 8/2007 | Miles et al. |
| 2007/0208228 A1 | 9/2007 | Pavento |
| 2007/0290369 A1 | 12/2007 | Hasegawa |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0167574 A1 | 7/2008 | Farquhar et al. |
| 2008/0183044 A1 | 7/2008 | Colleran |
| 2008/0183214 A1 | 7/2008 | Copp |
| 2008/0221473 A1 | 9/2008 | Calancie et al. |
| 2008/0234550 A1 | 9/2008 | Hawkes |
| 2009/0018399 A1 | 1/2009 | Martinelli |
| 2009/0018610 A1 | 1/2009 | Gharib et al. |
| 2009/0054804 A1 | 2/2009 | Gharib et al. |
| 2009/0062619 A1 | 3/2009 | Bjork |
| 2009/0069635 A1 | 3/2009 | Gephart |
| 2009/0076516 A1 | 3/2009 | Lowry |
| 2009/0105547 A1 | 4/2009 | Vayser |
| 2009/0105604 A1 | 4/2009 | Bertagnoli et al. |
| 2009/0124860 A1 | 5/2009 | Miles et al. |
| 2009/0177112 A1 | 7/2009 | Gharib et al. |
| 2009/0192403 A1 | 7/2009 | Gharib et al. |
| 2009/0264710 A1 | 10/2009 | Chana |
| 2010/0137690 A1* | 6/2010 | Miles et al. ............ 600/202 |
| 2010/0160738 A1 | 6/2010 | Miles |
| 2010/0273738 A1 | 10/2010 | Valcke et al. |
| 2010/0312068 A1 | 12/2010 | Dalton |
| 2010/0312103 A1 | 12/2010 | Gorek et al. |
| 2011/0137130 A1 | 6/2011 | Thalgott |
| 2011/0144450 A1 | 6/2011 | Paolitto |
| 2011/0172494 A1 | 7/2011 | Bass |
| 2011/0224497 A1 | 9/2011 | Weiman |
| 2011/0237902 A1 | 9/2011 | Rosen |
| 2011/0301421 A1 | 12/2011 | Michaeli |
| 2011/0301422 A1 | 12/2011 | Woolley |
| 2011/0301423 A1 | 12/2011 | Koros |
| 2012/0046527 A1 | 2/2012 | Cianfrani |
| 2012/0083662 A1 | 4/2012 | Hamada |
| 2012/0109004 A1* | 5/2012 | Cadwell ............ 600/554 |
| 2012/0130180 A1 | 5/2012 | Pell |
| 2012/0136392 A1 | 5/2012 | Keegan |
| 2012/0203070 A1 | 8/2012 | Crenshaw |
| 2012/0245431 A1 | 9/2012 | Baudouin |
| 2012/0245432 A1 | 9/2012 | Karpowicz |
| 2012/0283521 A1 | 11/2012 | Smith |
| 2012/0330106 A1 | 12/2012 | Wright |
| 2013/0123581 A1 | 5/2013 | Fritzinger |
| 2013/0158359 A1 | 6/2013 | Predick |
| 2013/0190575 A1 | 7/2013 | Mast |
| 2013/0261401 A1 | 10/2013 | Hawkins |
| 2014/0024900 A1 | 1/2014 | Capote |
| 2014/0066718 A1 | 3/2014 | Fiechter |
| 2014/0073857 A1 | 3/2014 | Dodson |
| 2014/0128979 A1 | 5/2014 | Womble |
| 2014/0135584 A1 | 5/2014 | Lee |

FOREIGN PATENT DOCUMENTS

| | | |
|---|---|---|
| DE | 4425652 | 2/1996 |
| EP | 0951868 | 10/1999 |
| EP | 1829488 | 9/2007 |
| JP | 3187929 | 12/2013 |
| WO | WO-9320741 | 10/1993 |
| WO | WO-03017847 | 3/2003 |
| WO | WO-2007002405 | 1/2007 |
| WO | WO-2010121291 | 10/2010 |
| WO | WO-2010125598 | 11/2010 |
| WO | WO-2010136860 | 12/2010 |
| WO | WO-2012093368 | 7/2012 |
| WO | WO-2013000105 | 1/2013 |

OTHER PUBLICATIONS

"Nerve Proximity and Status Detection System and Method," International Search Report from International Application No. PCT/US01/18606, dated Oct. 18, 2001, 6 pages.

"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.

"Systems and Methods for Performing Surgery Procedures and Assessments," International Search Report from International Application No. PCT/US02/30617, dated Jun. 5, 2003, 4 pages.

"Systems and Methods for Performing Percutaneous Pedicle Integrity Assessments," International Search Report from International Application No. PCT/US02/35047, dated Aug. 11, 2003, 5 pages.

"System and Methods for Determining Nerve Direction to a Surgical Instrument," International Search Report from International Application No. PCT/US03/02056, dated Aug. 12, 2003, 5 pages.

"Systems and Methods for Performing Neurophysiologic Assessments During Spine Surgery," International Search Report from International Application No. PCT/US06/03966, dated Oct. 23, 2006, 5 pages.

"Multi-Channel Stimulation Threshold Detection Algorithm for Use in Neurophysiology Monitoring," International Search Report from International Application No. PCT/US06/37013, dated Mar. 19, 2007, 6 pages.

"Neurophysiologic Monitoring System," International Search Report and the Written Opinion from International Application No. PCT/US08/04427, dated Jul. 28, 2008, 6 pages.

"Surgical Access System and Related Methods," International Search Report from International Application No. PCT/US2011/001489, dated Dec. 13, 2011, 3 pages.

"Surgical Access System and Related Methods," Written Opinion from International Application No. PCT/US2011/001489, dated Dec. 13, 2011, 7 pages.

"Neurovision SE Nerve Locator/Monitor," RLN Systems Inc. Operator's Manual, 1999, 22 pages.

Balzer, et al., "Simultaneous Somatosensory Evoked Potential and Electromyographic Recordings during Lumbosacral Decompression and Instrumentation Technique Application," Neurosurgery 1998, 42:1318-1325.

Banoczi, "Update on Anesthetic and Metabolic Effects During Intraoperative Neurophysiological Monitoring (IONM)," Am J END Technol 2005, 45:225-239.

Bednarik, et al., "The Value of Somatosensory- and Motor-Evoked Potentials in Predicting and Monitoring the Effect of Therapy in Spondylotic Cervical Myelopathy," Spine 1999, 24(15):1593-1598.

Bendersky, et al. "Monitoring lumbar plexus integrity in extreme lateral transpsoas approaches to the lumbar spine: a new protocol with anatomical bases," Eur Spine J 2015, published online, DOI 10.1007/s00586-015-3801-9.

Calancie and Molano, "Alarm Criteria for Motor-Evoked Potentials," Spine 2008 33(4):406-414.

Calancie et al., "Stimulus-Evoked EMG Monitoring During Transpedicular Lumbosacral Spine Instrumentation," Spine, 1994, 19(24): 2780-2786.

Calancie, et al., ""Threshold-level" multipulse transcranial electrical stimulation of motor cortex for intraoperative monitoring of (56) References Cited

OTHER PUBLICATIONS spinal motor tracts: description of method and comparison to somatosensory evoked potential monitoring," J Neurosurg 1998, 88:457-470.
Calancie, et al., "Threshold-level repetitive transcranial electrical stimulation for intraoperative monitoring of central motor conduction," J Neurosurg (Spine 1) 2011, 95:161-168.
Deletis, et al., "Neurophysiological mechanisms underlying motor evoked potentials in anesthetized humans. Part 1. Recovery time of corticospinal tract direct waves elicited by pairs of transcranial electrical stimuli," Clin Neurophysiol 2001, 112:438-444.
Deletis, et al., "Neurophysiological mechanisms underlying motor evoked potentials in anesthetized humans. Part 2. Relationship between epidurally and muscle recorded MEPs in man," Clin Neurophysiol 2001, 112:445-452.
Deutsch, et al., "Somatosensory evoked potential monitoring in anterior thoracic vertebrectomy," J Neurosurg (Spine2) 2000, 92:155-161.
Devlin and Schwartz, "Intraoperative Neurophysiologic Monitoring During Spinal Surgery," J Am Acad Orthop Surg 2007, 15(9):549-560.
Ginsburg, et al., "Postoperative paraplegia with preserved intraoperative somatosensory evoked potentials," J Neurosurg 1985, 63:296-300.
Gokaslan, et al., "Intraoperative Monitoring of Spinal Cord Function Using Motor Evoked Potentials via Transcutaneous Epidural Electrode During Anterior Cervical Spinal Surgery," J Spinal Disord 1997, 10(4):299-303.
Gunnarsson, et al., "Real-Time Continuous Intraoperative Electromyographic and Somatosensory Evoked Potential Recordings in Spinal Surgery: Correlation of Clinical and Electrophysiologic Findings in a Prospective, Consecutive Series of 213 Cases," Spine 2004, 29(6):677-684.
Holland et al., "Higher Electrical Stimulus Intensities are Required to Activate Chronically Compressed Nerve Roots. Implications for Intraoperative Electromyographic Pedicle Screw Testing," Spine, 1998, 23(2): 224-227.
Jones, et al., "Two cases of quadriparesis following anterior cervical discectomy, with normal perioperative somatosensory evoked potentials," J Neurol Neurosurg Psychiatry 2003, 74:273-276.
Kamel, et al., "The Use of Somatosensory Evoked Potentials to Determine the Relationship Between Patient Positioning and Impending Upper Extremity Nerve Injury During Spine Surgery: A Retrospective analysis," International Anesthesia Research Society 2006, 102:1538-1542.
Kombos, et al., "Monitoring of intraoperative motor evoked potentials to increase the safety of surgery in and around the motor cortex," J Neurosurg 2001, 95:608-614.
Kombos, et al., "Impact of Somatosensory Evoked Potential Monitoring on Cervical Surgery," J Clin Neurophys 2003, 20(2): 122-128.
Kraft, et al., "Somatosensory Evoked Potentials: Clinical Uses," Muscle Nerve 1998, 21:252-258.
Langeloo, et al., "A New Application of TCE-MEP: Spinal Cord Monitoring in Patients With Severe Neuromuscular Weakness Undergoing Corrective Spine Surgery," J Spinal Disord 2001, 14(5):445-448.
Langeloo, et al., "Transcranial Electrical Motor-Evoked Potential Monitoring During Surgery for Spinal Deformity," Spine 2003, 28(10) 1043-1050.

Legatt and Soliman, "Somatosensory Evoked Potentials: General Principles," eMedicine Neurology, 2006, http://emedicine.medscape.com/article/1139906-overview.
MacDonald, "Safety of Intraoperative Transcranial Electrical Stimulation Motor Evoked Potential Monitoring," J Clin Neurophys 2002, 19(5):416-429.
More, et al., "Cortical Evoked Potential Monitoring During Spinal Surgery: Sensitivity, Specificity, Reliability, and Criteria for Alarm," J Spinal Disord 1988, 1(1):75-80.
Nash, et al., "Spinal Cord Monitoring During Operative Treatment of the Spine," Clin Orthop Relat Res 1977, 126:100-105.
Nuwer, et al., "Somatosensory evoked potential spinal cord monitoring reduces neurologic deficits after scoliosis surgery: results of a large multicenter survey," Electroencephalogr Clin Neurophysiol 1995, 96:6-11.
Osburn, "A Guide to the Performance of Transcranial Electrical Motor Evoked Potentials. Part 1. Basic Concepts, Recording Parameters, Special Consideration, and Application," Am J END Technol 2006, 46:98-158.
Osburn, et al., "TCeMEPs offer Safe, Reliable Monitoring of Spinal Cord Motor Pathway Function during Cervical Procedures Performed for Post-traumatic Spine Injury," $17^{th}$ Annual Meeting of the American Society of Neurophysiological Monitoring Abstract Presentations, 2006.
Padberg, et al., "Somatosensory- and Motor-Evoked Potential Monitoring Without a Wake-Up Test During Idiopathic Scoliosis Surgery: An Accepted Standard of Care," Spine 1998, 23(12):1392-1400.
Pelosi, et al., "Combined monitoring or motor and somatosensory evoked potentials in orthopaedic spinal surgery," Clin Neurophysiol 2002, 113:1082-1091.
Silverstein, et al., "Saphenous Nerve Somatosensory Evoked Potentials: A Novel Technique to Monitor the Femoral Nerve During Transpsoas Lumbar Lateral Interbody Fusion," Spine 2014, 39(15)1254-1260.
Sloan and Heyer, "Anesthesia for Intraoperative Neurophysiologic Monitoring of the Spinal Cord," J Clin Neurophys 2002, 19(5):430-443.
Taylor, et al. "Chapter 5: The Role of Integrated Neurophysiologic Monitoring in XLIF®," eXtreme Lateral Interbody Fusion (XLIF®), $2^{nd}$ Ed., edited by J. Allan Goodrich, Ildemaro J. Volcan, 2013, pp. 45-57, Quality Medical Publishing, Inc., St. Louis, MO.
Toleikis, "Intraoperative Monitoring Using Somatosensory Evoked Potentials," J Clin Monit Comput 2005, 19:241-258.
Uribe, et al., "Electromyographic Monitoring and Its Anatomical Implications in Minimally Invasive Spine Surgery," Spine 2010, 35(26S)S368-S374.
Watanabe, et al., "Transcranial electrical stimulation through screw electrodes for intraoperative monitoring of motor evoked potentials," J Neurosurg 2004, 100:155-160.
Wiedemayer, et al., "False negative findings in intraoperative SEP monitoring: analysis of 658 neurosurgical cases and review of published reports," J Neurol Neurosurg Psychiatry 2004, 75:280-286.
Wiedemayer, et al., "The impact of neurophysiological intraoperative monitoring on surgical decisions: a critical analysis of 423 cases," J Neurosurg 2002, 96:255-262.
Zornow and Drummond, "Intraoperative Somatosensory Evoked Responses Recorded During Onset of the Anterior Spinal Artery Syndrome," J Clin Monit 1989, 5:243-245.

* cited by examiner

SYSTEMS AND METHODS FOR PERFORMING NEUROPHYSIOLOGIC MONITORING DURING SPINE SURGERY

CROSS REFERENCES TO RELATED APPLICATIONS

The present application is a non-provisional application claiming the benefit of priority under 35 U.S.C. §119(e) from commonly owned and U.S. Provisional Application Ser. No. 61/724,342 filed on Nov. 7, 2012 and entitled "Systems and Methods for Performing Neurophysiologic Monitoring During Spine Surgery," the entire contents of which are hereby incorporated by reference into this disclosure as if set forth fully herein. This application also incorporates by reference the entire contents of the following commonly owned Patents and Patent Applications: U.S. Pat. No. 7,905,840, issued on Mar. 15, 2011 and entitled "Surgical Access System and Related Methods;" and U.S. Pat. No. 8,255,045, issued Aug. 28, 2012 and entitled "Neurophysiology Monitoring System."

FIELD OF INVENTION

The present application pertains to devices and methods in the field of surgery, and more particularly spine surgery.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra and the like. Patients that suffer from such conditions usually experience extreme and debilitating pain, as well as diminished nerve function.

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques are gaining favor due to the fact that they involve accessing the surgical target site via incisions of substantially smaller size with greatly reduced tissue displacement requirements. This, in turn, reduces the pain, morbidity, and cost associated with such procedures. One such minimally invasive approach, a lateral trans-psoas approach to the spine, developed by NuVasive, Inc., San Diego, Calif. (XLIF®) has demonstrated great success in reducing patient morbidity, shortening the duration of hospitalization, and speeding recovery time if it is employed.

One example of a surgical retraction system and methods of use in a lateral trans-psoas approach to the spine is described in commonly owned U.S. Pat. No. 7,905,840, issued on Mar. 15, 2011 and entitled "Surgical Access System and Related Methods," the entire contents of which are incorporated by reference into this disclosure as if set forth fully herein. To create the lateral access corridor to the lumbar spine, the patient is positioned on his or her side and a surgical access system is advanced through an incision, into the retroperitoneal space, and then through the psoas muscle until the target spinal site (for example, a disc space between a pair of adjacent vertebral bodies) is reached. The surgical access system may include a sequential dilation assembly of increasing diameter and a tissue retraction assembly. The sequential dilation assembly is advanced to the target site first and the retractor assembly is then advanced to the target site over the sequential dilation system. One or more stimulating electrodes may be provided on the distal tip of each component of the surgical access system. Nerve monitoring may be performed while advancing each of the dilation and retraction assemblies to the target site to detect the presence of, and thereby avoid, nerves lying in the trans-psoas path to the target site.

Once the retractor assembly has been docked at a target site however, a nerve situated near any location along the length of a retractor blade (for example, a center (posterior) blade) might come into inadvertent contact with the blade which could cause the nerve to become compressed over the course of the surgical procedure. As such, information regarding the proximity, health, and status of nearby nerves (e.g., the ipsilateral femoral nerve, which is a "mixed" nerve) during maintenance of a lateral access corridor is desirable. Such information may include neurogenic responses (e.g. compound nerve action potential (CNAP) responses) obtained in response to stimulation of the sensory branches of the nerve and myogenic responses (e.g. compound muscle action potential (CMAP) responses or neuromuscular responses) obtained in response to stimulation of the motor branches of the nerve. Changes in these sensory and motor responses from baseline (i.e., prior to positioning of the retractor) could indicate that the nerve is potentially compromised at the location of the surgical site. A quick, reliable means of obtaining these sensory and motor responses could provide an advanced neuromonitoring capability that may further reduce the risk of neural compromise during spine surgery.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The femoral nerve localizer and related methods described herein boast a variety of inventive features and components that warrant patent protection, both individually and in combination.

Figure 1:
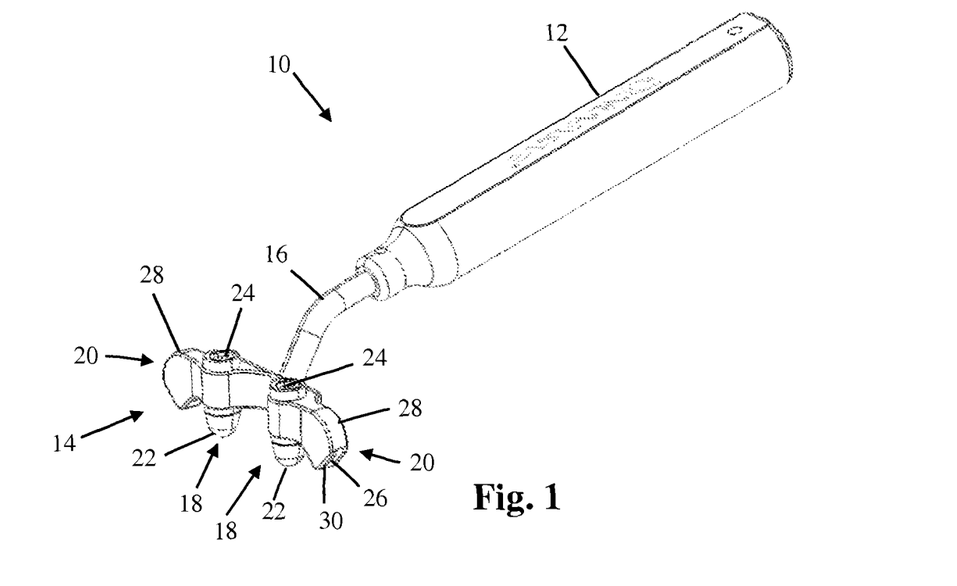
FIG. 1 is a perspective view of one example of a combination femoral nerve localizer and needle placement guide according to one embodiment of the present disclosure.
Figure 2:
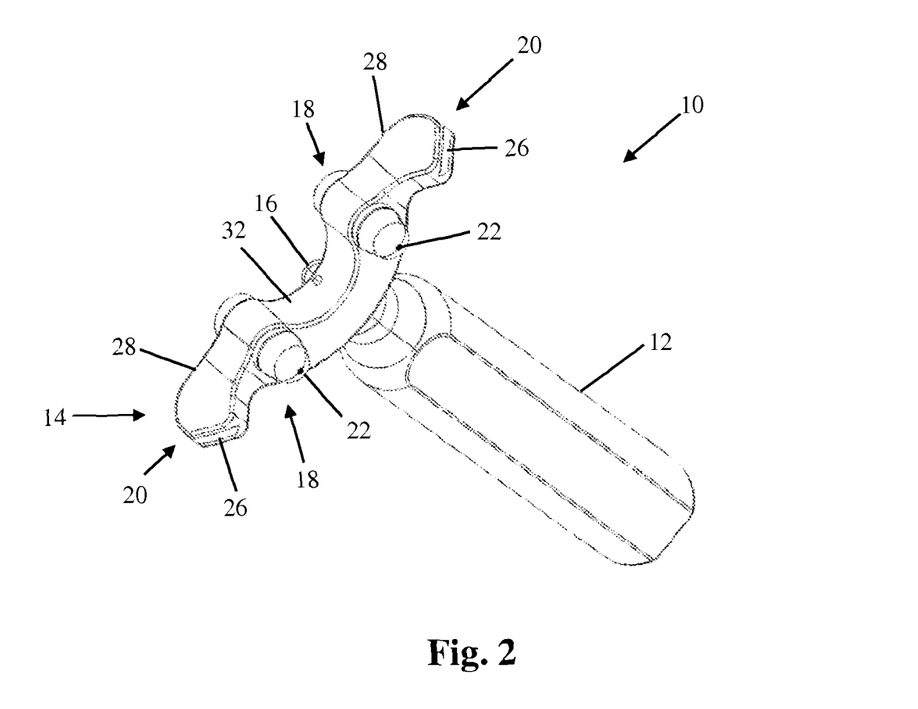
FIG. 2 is an alternative perspective view of the combination femoral nerve localizer and needle placement guide of FIG. 1.
Figure 3:
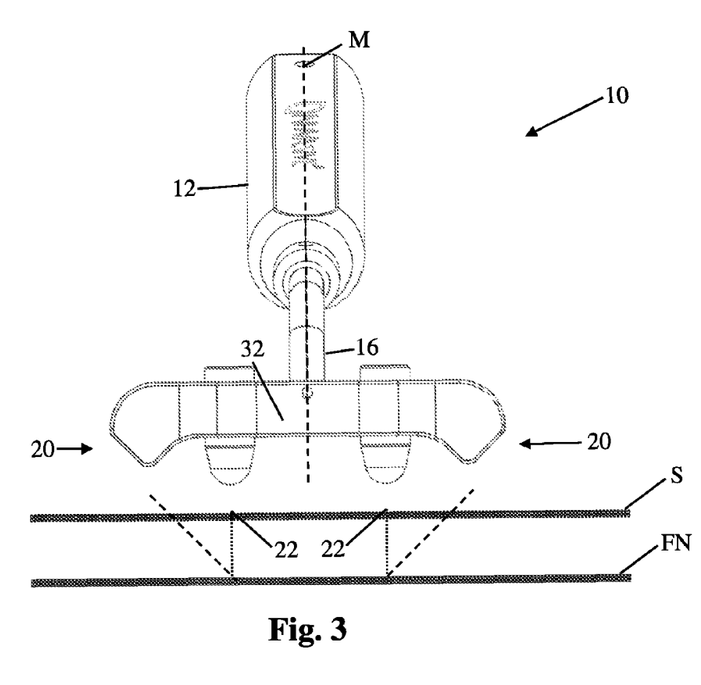
FIG. 3 is a front plan view of the combination femoral nerve localizer and needle placement guide of FIG. 1 in position relative to a patient's skin and femoral nerve.
Figure 4:
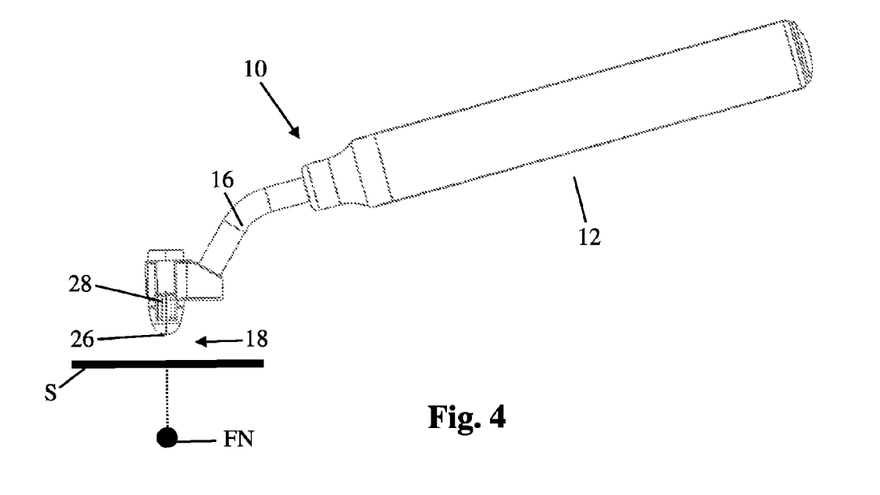
FIG. 4 is a side plan view of the combination femoral nerve localizer and needle placement guide of FIG. 1 in position relative to a patient's skin and femoral nerve.

FIGS. 1-4 illustrate an example of one embodiment of a combination femoral nerve localizer and needle placement guide instrument 10 (hereinafter "localizer/guide 10") for use in reliably localizing the femoral nerve for stimulating and recording purposes during neuromonitoring of a spinal surgical procedure, preferably a minimally-invasive lateral spine procedure. By way of example only, the localizer/guide 10 includes a handle 12 and a body 14 separated by a shaft 16 extending between the handle 12 and body 14. The handle 12 is sized and dimensioned to allow a user to comfortably position the localizer/guide 10 on the surface of a patient's body (e.g., at the ilioinguinal ligament). The body 14 is attached to the distal end of the shaft 16 and includes a pair of transcutaneous stimulation electrode units 18 and a pair of needle guides 20. One electrode unit 18 and needle guide 20 pair is provided on each side of the midline M (FIG. 3) as defined by the handle 12 and shaft 16. In the first embodiment shown, the electrode unit 18 and needle guide 20 pairs are arranged in a minor image orientation, however other configurations are possible without departing from the scope of this disclosure. Preferably, the body 14 is positioned offset from the handle 12 to enhance visibility of the patient's anatomy during femoral nerve localization and placement of the subdermal needles as will be described in greater detail below. To accomplish this, the shaft 16 may be provided as other than linear, for example the shaft 16 may be curved or may have a pair of linear portions connected by an angled joint portion as shown in FIG. 1.

The electrode unit 18 includes a transcutaneous stimulation electrode 22 in electrical communication with a lead receptacle 24. Each transcutaneous stimulation electrode 22 is provided at the distal end of the electrode unit 18 and is configured to contact the skin S (FIG. 3) and send/receive electrical stimuli therethrough. Each lead receptacle 24 is configured to receive a male plug portion of an lead cable (not shown) that connects the surface electrode 22 to a control unit of a neuromonitoring system, for example of the type shown and described in commonly owned U.S. Pat. No. 8,255,045, issued Aug. 28, 2012 and entitled "Neurophysiology Monitoring System," the entire contents of which is hereby incorporated by reference into this disclosure as if set forth fully herein. The two transcutaneous stimulation electrodes 20 function as a stimulation unit (i.e., one electrode acts as the anode, the other acts as the cathode) according to a preferred use. As the cathode is positioned directly over the femoral nerve, stimulation current is delivered from a neuromonitoring system (e.g. the neuromonitoring system of the above-referenced '045 patent) to the localizer/guide 10 which will activate the femoral nerve immediately deep to that electrode, and recording electrodes placed in muscle groups innervated by the femoral nerve will record neuromuscular responses on the neuromonitoring system.

The needle guide 20 is provided to accurately position a needle during the surgical procedure, for example a stimulating/recording needle electrode. The needle guide 20 includes a guide slot 26 positioned at a distal end of an arm member 28 extending laterally away from the midline M. The guide slot 26 is configured to receive a needle (not shown) therein. The distal end of the arm member 28 includes an angled distal surface 30 in which the guide slot 26 is formed. The angle of the distal surface 30 ultimately controls the angle (relative to the femoral nerve FN) at which the needle is inserted through the skin S. By way of example only, the angle may be a 30-degree angle. Other angles are possible without departing from the scope of this disclosure.

As previously mentioned, the electrode unit 18 and needle guide 20 pairs are positioned in a minor image orientation relative to one another. More specifically, the electrode units 18 are positioned between the needle guides 20 such that the angles of the angled surfaces 30 are convergent. This orientation not only maximizes the user's view of the anatomy, but it also enables the needles to be optimally placed distance from one another for recording purposes (for example, the distance between the needle tips may be 1 inch apart). The body 14 further includes a middle portion 32 extending between the electrode units 18. The shaft 16 is connected to the middle portion 32 of the body 14. In the example shown in FIGS. 1-4, the middle portion 32 has a generally concave curvature that also improves the view of the anatomy by the user.

Figure 5:
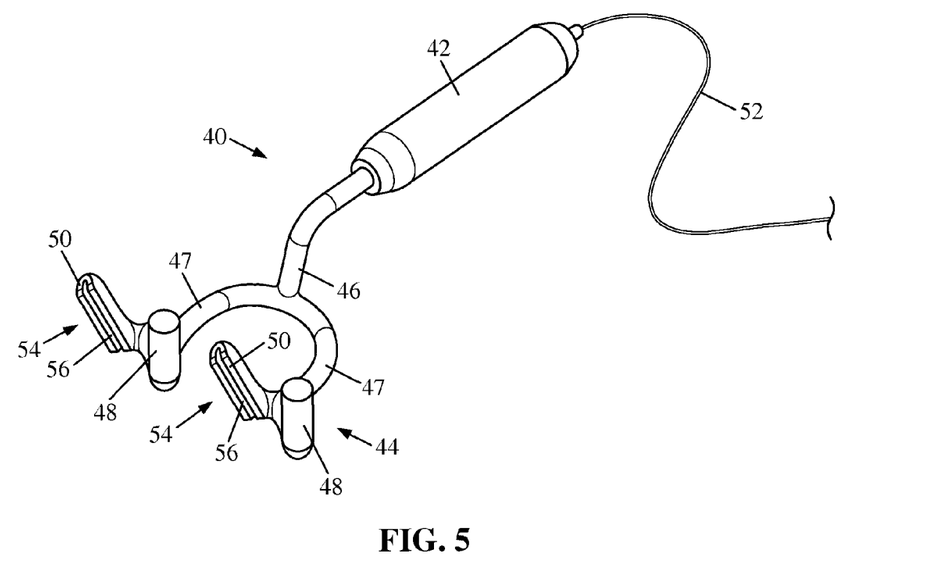
FIG. 5 is a perspective view of another example of a combination femoral nerve localizer and needle placement guide according to another embodiment of the present disclosure.
Figure 6:
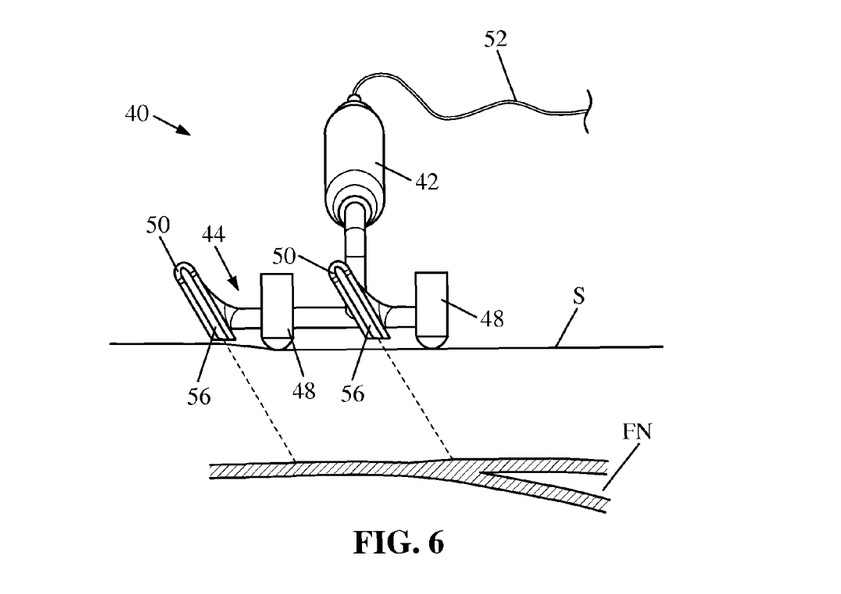
FIG. 6 is a front plan view of the combination femoral nerve localizer and needle placement guide of FIG. 5 in position relative to a patient's skin and femoral nerve.
Figure 7:
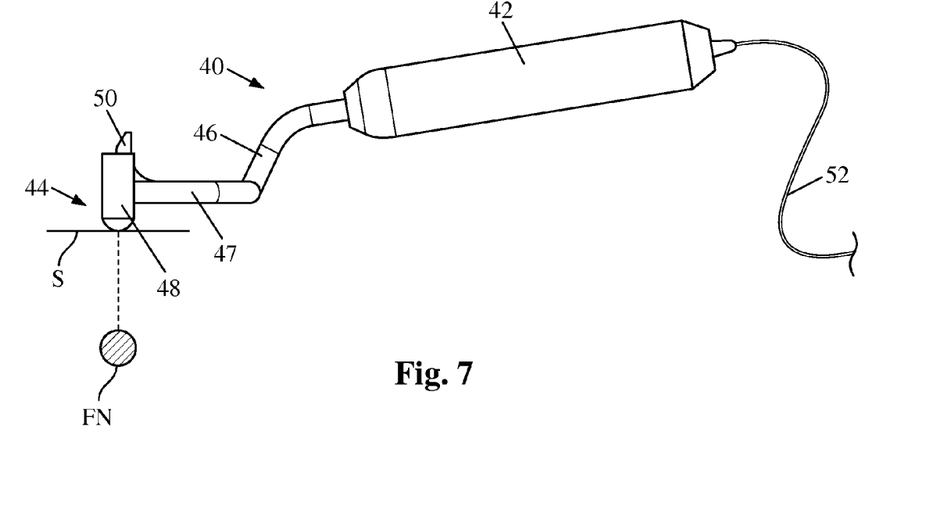
FIG. 7 is a side plan view of the combination femoral nerve localizer and needle placement guide of FIG. 5 in position relative to a patient's skin and femoral nerve.

FIGS. 5-7 illustrate an example of one embodiment of a combination femoral nerve localizer and needle placement guide instrument 40 (hereinafter "localizer/guide 40") for use in reliably localizing the femoral nerve for stimulating and recording purposes during neuromonitoring of a spinal surgical procedure, preferably a minimally-invasive lateral spine procedure. By way of example only, the localizer/guide 40 includes a handle 42 and a body 44 separated by a shaft 46 extending between the handle 42 and body 44. The handle 42 is sized and dimensioned to allow a user to comfortably position the localizer/guide 40 on the surface of a patient's body (e.g., at the ilioinguinal ligament). The body 44 is attached to the distal end of the shaft 46 and is generally a dual-pronged body is positioned offset from the handle 12 to enhance visibility of the patient's anatomy during femoral nerve localization and placement of the subdermal needles. The body 44 includes a pair of prongs 47 extending away from the shaft 46 in a generally arcuate manner. Each of the prongs 47 includes a transcutaneous stimulation electrode 48 and a needle guide 50.

The two transcutaneous stimulation electrodes 48 function as a stimulation unit (i.e., one electrode acts as the anode, the other acts as the cathode) according to a preferred use. As the cathode is positioned against the patient's skin S directly over the femoral nerve FN (FIG. 6), stimulation current delivered from a neuromonitoring system (e.g. the neuromonitoring system of the above-mentioned '045 patent) to the localizer/guide 40 will activate the femoral nerve immediately deep to that electrode 48. An electrode lead wire 52 extends from each electrode 48, through the handle 42 of the localizer/guide 40 and is capable of electrical communication with the stimulation circuitry of a neuromonitoring system (not shown) as will be explained in greater detail below. The needle guide 50 includes a guide barrel 54 and a slot 56 extending through the needle barrel 54 configured to receive a needle therein, for example a stimulating/recording needle electrode. The needle barrel 54 is generally cylindrical in shape with a central aperture extending between two ends. However, it is to be noted that the needle guide barrel 54 is not a closed cylinder—there is an elongated slot 56 extending between its two ends which is sized and dimensioned to allow the localizer/guide 40 to be safely removed from the needles once the needles are securely positioned at a predetermined location. The needle guide barrels 54 are also not positioned perpendicular to the skin or parallel to the transcutaneous stimulation electrodes 48. Instead, they are preferably angled, such that when a needle is inserted into the skin S through the barrel 54, it does so at an angle (e.g., a 30 degree angle) relative to the femoral nerve.

For the sake of clarity, the various methods described herein will be described in relation to the localizer/guide 10 described above with respect to FIGS. 1-4. However, it should be understood that either example embodiment described herein (or any combination of the disclosed features) may be used without departing from the scope of this disclosure. Furthermore, it should be appreciated that while the localizer/guide 10 and nerve localization method will be described with respect to the femoral nerve, other nerves may be localized without departing from the scope of this disclosure. According to one method of femoral nerve localization, the transcutaneous stimulation electrodes 22 of the localizer/guide 10 are placed on the surface of the patient's skin S along the ilioinguinal ligament. The neuromonitoring system may then apply a stimulation current to the electrodes 22 until the control unit detects a significant neuromuscular response in one or more muscles innervated by the femoral nerve (e.g., adductor longus, vastus lateralis, vastus medialis). This is the stimulation threshold intensity. The stimulation threshold intensity may then be ascertained at one or more additional sites along the ilioinguinal ligament and compared to the previous locations to determine the optimal stimulation/recording location for the femoral nerve FN. By way of example only, the optimal location may be the location along the femoral nerve with the lowest stimulation threshold intensity value or the location with the most responses from the muscles innervated by the femoral nerve. According to one or more implementations, the neuromonitoring system may utilize a stimulating hunting algorithm to quickly ascertain the stimulation threshold intensities (e.g., the hunting algorithms described the above-referenced '045 patent). Once the ideal location for the femoral nerve recording/stimulating site is ascertained as described above, the subdermal needle stimulating/recording electrodes may be positioned using the needle guides 20. Once positioned, the distal tip of each needle electrode will be directly beneath the transcutaneous stimulation electrode 22 at the idealized location for stimulating/recording from the femoral nerve.

With the location of the femoral nerve optimized and needle electrodes placed near the femoral nerve at that location, the neuromonitoring system may be used to 1) stimulate one or more locations inferior to the surgical site and record responses at one or more locations superior to the surgical site, and 2) stimulate one or more locations superior to the surgical site and record responses at one or more locations inferior to the surgical site.

According to a first example embodiment, the femoral nerve may be stimulated at the ilioinguinal ligament and the lumbar potential (LP) sensory responses may be recorded superior to the surgical site. According to a second embodiment, the femoral nerve may be stimulated at the ilioinguinal ligament and LP sensory responses may be recorded superior to the surgical site and/or AL, VL, VM responses may be recorded inferior to the surgical site. According to a third embodiment, the sensory tracts may be activated at the location of the LP electrodes and sensory responses may be obtained at the femoral nerve electrodes. According to a fourth embodiment, the sensory tracts may be activated at the location of the LP electrodes, the neurogenic potential may be obtained at the femoral nerve electrodes and motor responses may be recorded in the AL, VL, or VM. According to a fifth embodiment, a stimulation can occur at the surgical site (e.g., a stimulation signal can be elicited from an electrode integrated into or near a retractor blade, for example a retractor blade forming part of the retraction system in the above-referenced '840 patent) and the LP, FN, and neuromuscular responses may be obtained.

Optionally, the neuromonitoring system may either manually or automatically switch stimulating and recording capabilities from the inferior and superior locations, such that each stimulation site may also serve as a recording site.

It is to be appreciated that at least one and as many as all of the embodiments described in the preceding paragraph may be utilized in a given surgical procedure, alone or in combination. According to some implementations, the neuromonitoring system may automatically interleave stimulating and recording parameters between using each of the LP and FN sites as stimulating and recording sites. According to some implementations, a fixed stimulation threshold may be established and the amplitude and latencies of the neurogenic and/or myogenic responses may be tracked over time and compared to a baseline response (manually or automatically). By way of example only, if the amplitudes decrease below a pre-determined criteria or the latencies increase above a pre-determined criteria, it could be indicative of a change in the health and/or status of the femoral nerve across the surgical site. The user could be provided this information by the neuromonitoring system via one or more easy-to-interpret indicia. Further, according to yet other implementations, the neuromonitoring system may provide the user easy-to-interpret results as to the health and status of the femoral nerve. By way of example, this may be accomplished via one or more of color (e.g. R/Y/G), audio, visual, or textual indicators.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. For example, any of the features of a particular example described herein may be used with any other example described herein without departing from the scope of the present invention.

What is claimed is:

1. A surgical instrument configured to allow a user to localize a nerve and guide placement of first and second subdermal needle electrodes, comprising:
   a. a body portion comprising
      i. a first transcutaneous, surface stimulation electrode having a first longitudinal axis;
      ii. a second transcutaneous, surface stimulation electrode having a second longitudinal axis, and
      iii. at least first and second subdermal needle electrode guides,
   wherein said first subdermal needle electrode guide is positioned on a first arm stemming from and offset from said first transcutaneous, surface stimulation electrode, and said second subdermal needle electrode guide is positioned on a second arm stemming from and offset from said second transcutaneous, surface stimulation electrode, the first transcutaneous, surface stimulation electrode being positioned medially on the body portion, and the second transcutaneous, surface stimulation electrode being positioned distally on the body portion, said first and second transcutaneous, surface stimulation electrodes separated from one another by a distance and each including a distal skin contacting surface, and wherein said first subdermal needle electrode guide includes a first angled slot having a third longitudinal axis positioned at an angle relative to the first longitudinal axis of the first transcutaneous, surface stimulation electrode and wherein the second subdermal needle electrode guide includes a second angled slot having a fourth longitudinal axis positioned at an angle relative to the second longitudinal axis of the second transcutaneous, surface stimulation electrode, and wherein the first subdermal needle electrode guide is dimensioned to receive at least a portion of said first subdermal needle electrode therein, and wherein the second subdermal needle electrode guide is dimensioned to receive at least a portion of said second subdermal needle electrode therein, and
   b. a handle member connected to the body portion and configured to allow the user to position the surgical instrument.

2. The surgical instrument of claim 1, further comprising a shaft between the body portion and the handle member, wherein the body portion includes at least two prongs extending from the shaft, and the body portion is positioned offset from the handle.

3. The surgical instrument of claim 1, wherein the handle member defines a midline extending through and bisecting the surgical instrument.

4. The surgical instrument of claim 3, wherein the first transcutaneous, surface stimulation electrode is positioned on a first side of the midline, and the second transcutaneous, surface stimulation electrode is positioned on a second side of the midline.

5. The surgical instrument of claim 4, wherein the first subdermal needle electrode guide is positioned proximate to the first transcutaneous, surface stimulating electrode and distal with respect to the body portion, and the second subdermal needle electrode guide is positioned proximate to the second transcutaneous, surface stimulating electrode but medial to the body portion.

6. The surgical instrument of claim 5, wherein the first angled slot of the first subdermal needle electrode guide is parallel to the second angled slot of the second subdermal needle electrode guide.

7. The surgical instrument of claim 1, wherein the handle member is offset from the body.

8. The surgical instrument of claim 1, further comprising an electrical trace extending from the handle member.

9. The surgical instrument of claim 1, wherein the first and second angled slots of each of the at least first and second subdermal needle electrode guides are configured to position each of the first and second subdermal needle electrodes at an angle between 1 and 90 degrees relative to horizontal.

10. The surgical instrument of claim 1, further comprising a shaft extending between the body portion and handle member, wherein the body portion includes at least two prongs extending from the shaft.

11. The surgical instrument of claim 10, wherein the at least two prongs extend from the shaft in an arcuate manner.

* * * * *